United States Patent
Liu et al.

(10) Patent No.: US 10,540,760 B2
(45) Date of Patent: Jan. 21, 2020

(54) METHOD OF SEPARATING, IDENTIFYING AND CHARACTERIZING CRACKS IN 3D SPACE

(71) Applicant: SUN YAT-SEN UNIVERSITY, Guangdong (CN)

(72) Inventors: Jie Liu, Guangdong (CN); Jincheng Huang, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 1 day.

(21) Appl. No.: 15/633,762

(22) Filed: Jun. 27, 2017

(65) Prior Publication Data
US 2017/0372470 A1 Dec. 28, 2017

(30) Foreign Application Priority Data
Jun. 27, 2016 (CN) .......................... 2016 1 0494280

(51) Int. Cl.
*G06T 7/00* (2017.01)
*G06T 7/60* (2017.01)

(52) U.S. Cl.
CPC .............. *G06T 7/0004* (2013.01); *G06T 7/60* (2013.01)

(58) Field of Classification Search
USPC ........................................................ 382/109
See application file for complete search history.

(56) References Cited

U.S. PATENT DOCUMENTS

2014/0044315 A1* 2/2014 Derzhi ............... G06K 9/00624
382/109
2017/0273651 A1* 9/2017 Behrooz ................ A61B 6/505

OTHER PUBLICATIONS

Dare et al., "An Operational Application of Automatic Feature Extraction: The Measurement of Cracks in Concrete Structures," Photogrammetric Record, Apr. 2002, pp. 453-464.
Lee et al., "Automated image processing technique for detecting and analysing concrete surface cracks," Structure and Infrastructure Engineering, Jun. 2013, pp. 567-577.
Jahanshahi and Masri, "A new methodology for non-contact accurate crack width measurement through photogrammetry for automated structural safety evaluation," Smart Materials and Structures, Feb. 2013, pp. 1-12.
(Continued)

*Primary Examiner* — Justin P. Misleh
(74) *Attorney, Agent, or Firm* — JCIPRNET

(57) ABSTRACT

The present invention discloses a method of separating, identifying and characterizing cracks in rocks or other materials in three-dimensional (3D) space, which processes as follows to a volumetric digital image: 1) preprocessing digital image; 2) statistically analyzing basic information of the image including porosity, connectivity of each pore, and position, size, orientation and anisotropy of each pore-structure; 3) filtration: removing non-crack structures; 4) smoothening: smoothening and mending the image; 5) thinning: thinning the void structure into a thickness d (2 to 3 voxels recommended) in a direction with shortest extension; 6) separation: separating intersected cracks in a crack network by breaking the connections; 7) combination: combining those elongated cracks that are disconnected in the last step, and restoring cracks to the thickness before thinning, and eventually giving out the characterization of the cracks.

8 Claims, 12 Drawing Sheets

(56) References Cited

OTHER PUBLICATIONS

Arena et al., "A new computational approach to cracks quantification from 2D image analysis: Application to micro-cracks description in rocks," Computers & Geosciences, Jan. 2014, pp. 106-120.
Song et al., "Skeleton and fractal law based image recognition algorithm for concrete crack," Chinese Journal of Scientific Instrument, Aug. 2012, pp. 1850-1855.
Wang et al., "Automatic Recognition of Cracks in Tunnel Lining Based on Characteristics of Local Grids in Images," Chinese Journal of Rock Mechanics and Engineering, May 2012, pp. 991-999.
Delle Piane et al., "Micro-crack enhanced permeability in tight rocks: An experimental and microstructural study," Tectonophysics, Oct. 2015, pp. 149-156.
Liu et al., "Computational challenges in the analyses of petrophysics using microtomography and upscaling: A review," Feb. 2016, pp. 107-117.
Ketcham et al., "Nondestructive high-resolution visualization and measurement of anisotropic effective porosity in complex lithologies using high-resolution X-ray computed tomography," Journal of Hydrology, Feb. 2005, pp. 92-106.
Nakashima and Kamiya, "Mathematica Programs for the Analysis of Three-Dimensional Pore Connectivity and Anisotropic Tortuosity of Porous Rocks using X-ray Computed Tomography Image Data," Journal of Nuclear Science and Technology, Sep. 2007, pp. 1233-1247.
Liu et al., "Improved estimates of percolation and anisotropic permeability from 3-D X-ray microtomography using stochastic analyses and visualization," Geochemistry Geophysics Geosystems, May 2009, pp. 1-13.
Liu et al., "From characterisation of pore-structures to simulations of pore-scale fluid flow and the upscaling of dermeability using microtomography: A case study of heterogeneous carbonates," Journal of Geochemical Exploration, Feb. 2014, pp. 84-96.

\* cited by examiner

METHOD OF SEPARATING, IDENTIFYING AND CHARACTERIZING CRACKS IN 3D SPACE

CROSS-REFERENCE TO RELATED APPLICATION

This application claims the priority benefit of China application serial no. 201610494280.5, filed on Jun. 27, 2016. The entirety of the above-mentioned patent application is hereby incorporated by reference herein and made a part of this specification.

TECHNICAL FIELD

The present invention relates to a field of crack identification, and more particularly, to a method of separating, identifying and characterizing intersected cracks in three-dimensional (3D) space.

BACKGROUND

Cracks are commonly developed in rocks (and other brittle materials), which are caused by forces and damage, and have significant effects on subsequently material strength. Meanwhile, the cracks play an important role in fluid migration (e.g. groundwater, oil and gas). Characterization or description of the cracks is the basis of the study of the relationships between mechanics, fluid mechanics and the geometry of cracks. Quantitative characterization of the cracks generally includes main parameters of the crack, such as length, width, orientation, and distribution density. For a crack network composed of intersected cracks, characterization of the cracks firstly needs to separate individual cracks from the network one by one.

Existing observations of cracks mostly use field outcrops, core samples, and also thin sections of rocks. These observations can only extract two-dimensional (2D) characteristics of cracks on the observed surface. Separation and identification of individual cracks based on 2D images or data are relatively easy to achieve because the images and data are straightforward. For example, given a 2D crack network shown in FIG. 1A and FIG. 1B, obviously, it is very easy to carry out the separation and identification of individual cracks manually. A 2D crack network with intersected and interconnected fractures, as shown in FIG. 1A, can be separated as a combination of individual cracks, and as shown in FIG. 1B, represents individual cracks after separation and identification.

When the problem is extended to three dimensions, since the distribution and intersection of the cracks in the 3D space may be extremely complex, the separation and identification one by one of the individual cracks, which the characterization of the cracks firstly needs to achieve, encounters very technical difficulties. From the complex 3D crack network shown in FIG. 2, it can be seen that the separation and identification of each of the individual cracks will be a huge challenge.

Separation and Identification of 3D Cracks

Scholars have conducted preliminary studies on identification and characterization of the 2D cracks. Dare et al. (2002) proposed a method of measuring width of an individual crack using digital images of concrete surfaces. Lee et al. (2013) proposed a method also based on digital images of concrete surfaces that automatically extracts the characteristics of the width, length, and direction of cracks, and uses a neural network to identify the cracking model. Jahanshahi and Masri (2013) also proposed a method using image thinning and distance transform techniques to complete extraction of characteristics of cracks from images. Arena et al. (2014) realized the separation and quantification of intersected cracks in a 2D image by identifying intersections. Among the domestic scholars, Yang Song et al. (2012) proposed skeleton and fractal law based image recognition algorithm for concrete crack according to the difference between the crack and other elements in fractal feature. Wang Pingrang et al. (2012) proposed recognition of cracks based on characteristics of local grids in images, which automatically calculated the trend, length and width of the crack in the recognition process.

It should be pointed out that the above studies are based on 2D images, where only one case of identification and characterization study of 3D crack can be seen. Delle Piane et al. (2015) first used the particle separation function of Avizo® software to separate the particles in the heated marble samples with complete particle morphology; and then determined an intersection of three (or more) particles as a crack junction, and partitioned the cracks that form a network using these intersections. Successful separation of cracks of this attempt is totally dependent on the enclosed form of cracks. It is noted that the conjunction point of the cracks in this method is determined by the intersection of three (or more) particles, and thus the method is only applicable to the crack system that constitutes enclosed surfaces. It is not applicable for a crack network in a general case (such as a very simple case: two intersecting cracks without reaching the boundary of the model). In addition, this method has to be operated by means of the particle partitioning function of the Avizo® software. On the one hand, the crack network formed by separation boundary obtained by the particle separation of the Avizo® software may be quite different from the crack network which can be recognized in the original image; on the other hand, the Avizo® software can handle volumes that are limited in size (Liu et al. 2016).

Characterization of Cracks

Since the development of micro-tomography (or micro-computed tomography, micro-CT), there are more studies focused on porous media, and the techniques and methods of fine characterization for pore-structures have been well developed (Ketcham & Iturrino, 2005; Nakashima & Kamiya, 2007, Liu et al., 2009, 2014).

The quantitative characterization of crack structures is difficult to develop because the separation and identification of the individual cracks fail to be achieved. Once individual cracks are separated and identified, there is no difficulty in obtaining the main parameters of the crack such as length, width, orientation, and density. Delle Piane et al. (2015), after realized the separation of the cracks with specific structure in their samples, used the statistical function of the Avizo® software to give out corresponding crack characterization and statistical results.

After the separation and identification of the cracks are achieved, each crack is recognized as a "cluster" (which has a unique label and can be understood as an identified void-structure). At this time, the characterization program ctsta10.f90 of microtomographic data may be used for crack characterization. The program was originally used for the fine characterization of pore structures, with output parameters including: porosity, specific surface area, and the size, location, shape, orientation of individual clusters (structures).

In view of this, the realization of the characterization of the cracks in a 3D space has a key technology lying in the separation and identification of the individual cracks.

SUMMARY OF THE INVENTION

In order to overcome the deficiencies of the prior arts, the present invention proposes a method of separating, identifying and characterizing of cracks in a 3D space.

In order to solve the above-described technical problems, the technical solution adopted in the present invention is as follows:

a method of separating, identifying and characterizing of cracks in 3D space, which processes as follows to digital images so as to perform the separation, identification and the characterization of the cracks in a 3D space:

1) preprocessing a 3D digital image to provide binary data for the following analyses;
2) statistically analyzing basic information of the digital image: the basic information of the image data includes porosity, connectivity, and position, size, orientation and anisotropy of each void structure;
3) filtration: removing non-crack structures in the digital image;
4) smoothening: smoothening and mending the digital image;
5) thinning: thinning the void structure into a thickness d in a most narrow direction in three-dimensions;
6) separation: separating intersected cracks in a crack network by detecting the intersection and breaking the connection (independent from enclosed crack-surfaces);
7) combination: unifying the labels of segments of a crack that are disconnected in the last step, merging very small structures that are formed during the separation to a nearby large structure, restoring the thickness of cracks, and eventually analyzing porosity, connectivity, and position, size, orientation and anisotropy of each void structure, achieving the separation, identification and characterization of the cracks in the 3D space.

Preferably, a compute mode of the anisotropy of the pore mentioned in step 2) is as follows:

for a void structure containing n voxels (volumetric pixels), each voxel forms a vector from a center point of the cluster to a current position i presented as $a_i = (a_{xi}, a_{yi}, a_{zi})^T$, and coordinates of a center of the void is calculated by a mean value of all point coordinates in the void-structure. Then an anisotropy of the void-structure can be represented by an orientation matrix R:

$$R = \sum_{i=1}^{n} a_i a_i^T = \begin{bmatrix} \sum_{i=1}^{n} a_{xi}^2 & \sum_{i=1}^{n} a_{xi}a_{yi} & \sum_{i=1}^{n} a_{xi}a_{zi} \\ \sum_{i=1}^{n} a_{xi}a_{yi} & \sum_{i=1}^{n} a_{yi}^2 & \sum_{i=1}^{n} a_{yi}a_{zi} \\ \sum_{i=1}^{n} a_{xi}a_{zi} & \sum_{i=1}^{n} a_{yi}a_{zi} & \sum_{i=1}^{n} a_{zi}^2 \end{bmatrix}$$

The matrix has three eigenvalues $\tau_1 < \tau_2 < \tau_3$ and corresponding eigenvectors $\mu_1, \mu_2, \mu_3$. An isotropic index $I = \tau_1/\tau_3$ and an elongation index $E = 1 - \tau_1/\tau_3$ are used to define the anisotropy of the pore. When $E \to 0$ and $I \to 1$, it indicates that the pore is isotropic.

In particular, a cluster is an independent structure composed of voxel of a same material connected by common surfaces in binary data. If an individual voxel is material 1, and there is no common plane with other voxels around that are material 1, then this voxel is a cluster. A plurality of voxels that are identified the same material can be connected by common planes one by one into a large and very complex cluster, and a plurality of intersected cracks also constitute a cluster.

In its original definition, a cluster is a structure that is interconnected inside but not connected with an outside world.

Preferably, a process of the filtration mentioned in step 3) is as follows: when the cluster meets a filter criterion, modifying material identities of all the voxels in the cluster, that is, modifying a vois identity 1 to 0, which represents that this small void structure is changed into a part of a rock, and is not exist in a subsequent analysis, the identity 1 representing the void structure, the identity 0 representing a part of the rock.

Preferably, a process of the smoothening mentioned in step 4) is as follows: performing smoothening and mending operations to the filtered digital image, which specifically use a closing operation in mathematical morphology to realize smoothening and mending of the image, the morphological closing operation including a dilation operation and a following erosion operation.

The dilation operation is a basic operation in morphology, an operation to evaluate local maximum; firstly, a previously defined structuring element B is convolved with an image A, that is, a maximum value of a gray scale of the pixel in a region of the image A covered by the structuring element B is calculated first, and the maximum value is assigned to a pixel specified by an origin of the structuring element B. This causes a highlighted area of the grayscale image to expand gradually, which, for a binary image, it is also equivalent to process an OR operation to the structuring element B and the image A, and a result of the operation determines a value of the pixel specified by the origin.

In particular, the structuring element is a structure in which the origin is centered, and it shape and size can be any.

The erosion operation is a basic operation in morphology, and is mutually dual to the dilation, erosion being essentially an operation to evaluate local minimum, having an operation method similar to the dilation, which uses the local minimum for assigning to a pixel specified by the origin of the structuring element B, and this operation causes the highlighted area of the grayscale image to reduce gradually. For the binary image, it is also equivalent to process an AND operation to the structuring element B and the image A, and a result of the operation determines a value of the pixel specified by the origin. Since the erosion and the dilation are mutually dual, a complementary set of the image A being eroded by the structuring element B equals to a complementary set of the image A being dilated by the structuring element B.

The morphological closing operation processes a dilation operation to the filtered image first, and then processes an erosion operation.

Preferably, a process of the thinning mentioned in step 5) is as follows: determining whether a current point is a void point needed to be processed; for the void point, calculating its extension in three directions, that is, checking point by point in the both sides (positive and negative of the axis) of three directions of x, y, z; if encountering a non-void point on one of the directions, then stopping the check on the direction and recording an extension length of each axis; after finishing checking the three directions, selecting the direction with smallest extension length as the direction to be thinned; then thinning this direction from the boundary to the center to a thickness of d (d could be any number and recommended to be 2 or 3) voxels; except the d (2 or 3) voxels, assignments of other voxels on this direction are all changed, that is, identified as 0, making them a part of the rock, and recording relevant information (thinning direction and thinning voxels); after completing the processing, proceeding to calculation of a next point.

Preferably, the separation mentioned in step 6) is separating the thinned data, so that the originally interlaced structures are separated and become independent structures, a specific process of the separation being as follows:

(1) using a local grid for point-by-point process from the three-dimensions; generating two 2D square local grids in the three directions, respectively, with a current processing pixel as a center, and two given analysis radiuses (actually, half-side-lengths of square grids), a large one and a small one, each point-by-point process uses only image information in the grid; taking the current processing pixel as an origin, with two local grids being divided into four quadrants by the origin; for the local grids with large outer radius, if two structures in any two quadrants are linear and the angle between them meets a pre-defined criterion (an adjustable input parameter), while a number of void voxels contained in a corresponding quadrant in the grid with smaller inner radius is not less than a preset number (in the present invention, the number is also set as an adjustable input parameter, in order to facilitate a specific operation of different crack conditions), then they are taken as a projection of two cracks with different intersecting directions on a current section, thus changing a pixel value at the current origin, making it a part of the rock;

(2) for a 3D image, the processing step is to proceed from the three directions in turn until it is determined whether the current pixel should be classified as the rock.

Preferably, a process of the combination mentioned in step 7) is as follows: firstly determining whether each void structure should be combined with another void structure, with determining conditions including: i) whether normal directions of the two void structures are approximately parallel; ii) whether they originally belong to the same void before the separation step; iii) whether their normal lines are perpendicular to a line of their centers. If the above conditions are satisfied, then they are determined as should be combined. The combination process is to assign the same cluster identity to the void structures each belonging to different cluster identities after the separation step under the premise of being determined as belonging to the same crack.

Preferably, the method further comprises: based on the information recorded in the thinning step, restoring the shape of each void to that before thinning; obtaining a final processing result. In the final result, each cluster represents one crack (different from its original definition, a cluster by this step maybe not interconnected thoroughly but is broken to multi-pieces), and is restored to the state before thinning. The position, size, surface area, orientation of each cluster can be accurately calculated and expressed, in order to achieve the precise characterization of the cracks.

Compared with the prior arts, the present invention has following beneficial effects: the present invention identifies individual cracks from the 3D complex crack network using a separating methods independent from the enclosed surfaces of cracks, restores the thickness of cracks and the extending dimensions broken while separating, and thereby realizes the characterization of the cracks. The method provides important technical supports for carrying out researches such as crack morphology, permeability and mechanical response, and scaling up.

BRIEF DESCRIPTION OF THE DRAWINGS

FIG. 1A and FIG. 1B are schematic views of the 2D crack network that is intersected, wherein FIG. 1A is a schematic view of that before identification, and FIG. 1B is a schematic view of each crack being performed separation and identification as a mixture of individual cracks, where different grey-scales represent different cracks.

FIG. 11A and FIG. 11B are schematic views of the separation process, wherein FIG. 11A shows a state before disconnection and FIG. 11 B shows that the intersection set of the cracks is disconnected.

FIG. 1.8 is a schematic view of a typical case 1.

DETAILED DESCRIPTION OF THE PREFERRED EMBODIMENT

The present invention is further described below in combination with the accompanied drawings, but implementations of the present invention are not limited hereto.

Figure 3:
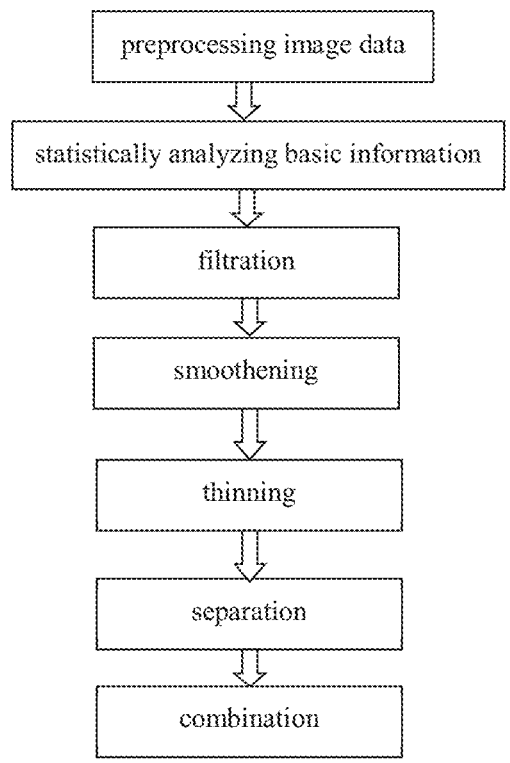
FIG. 3 is the workflow of the invention of separating, identifying and characterizing of cracks.

Micro-CT images are commonly asked for routine preprocessing, including smoothening, denoising, edge cutting, image segmentation (identification of crack or pore). Thus the actual work requires 7 steps, and there are 6 main steps after the image segmentation, as shown in FIG. 3, that is:

0) preprocessing digital image 1) statistically analyzing basic information: basic information of the digital image, such as porosity, connectivity, structure anisotropy, etc.

2) filtration: removing non-crack structure in the data, such as very small structures or structures with strong isotropic 3) smoothening: smoothening and mending the digital image 4) thinning: thinning the void structure into a certain thickness in a most narrow direction in three-dimensions 5) separation: separating intersected cracks in a crack network by detecting the intersection and breaking the connection (independent from enclosed crack-surfaces)

6) combination: unifying the labels of segments of a crack that are forcibly disconnected in the last step, merging very small structures that are formed during the separation a nearby large structure, restoring the shape of each void to that before thinning, and eventually analyzing porosity, connectivity, and position, size, orientation and anisotropy of each void structure, finishing the separation, identification and characterization of the cracks in the 3D space.

Data preprocessing is briefly introduced below, and the 6 main implementation steps are then introduced.

Figure 1A:
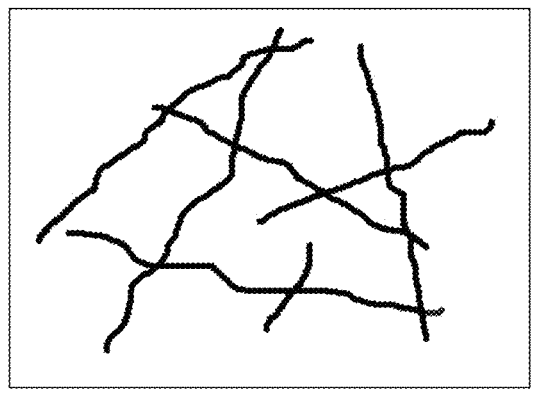
Figure 1B:
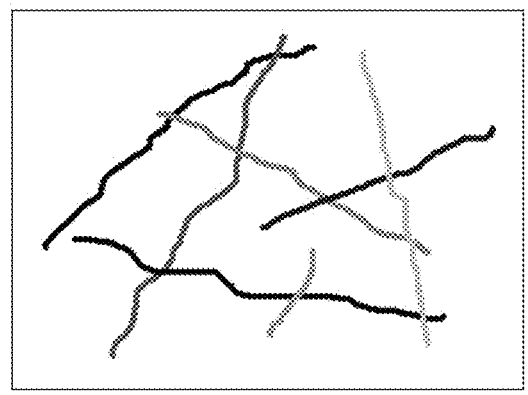
Figure 2:
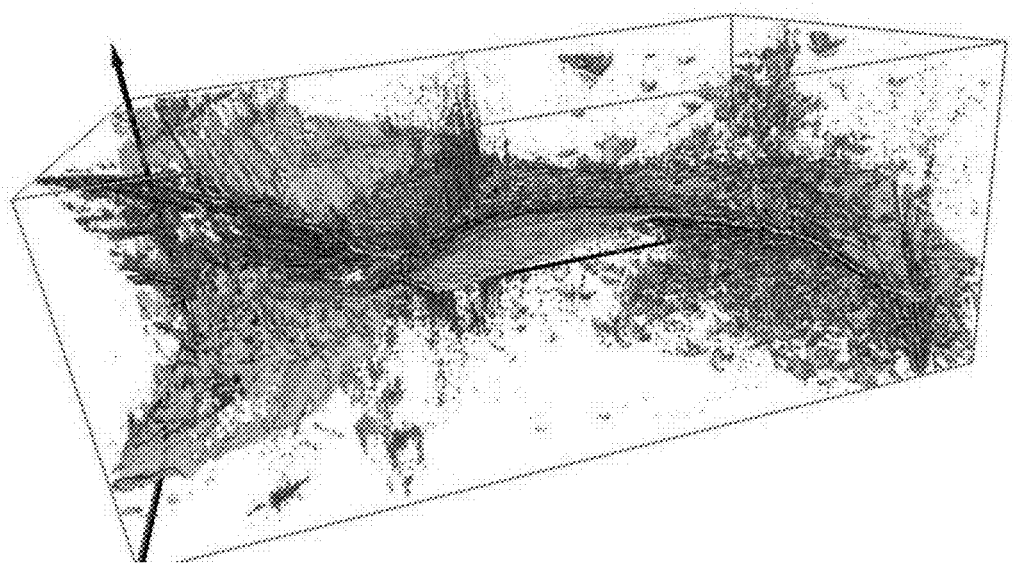
FIG. 2 is a schematic view of the 3D crack structure of a rock sample.
Figure 4:
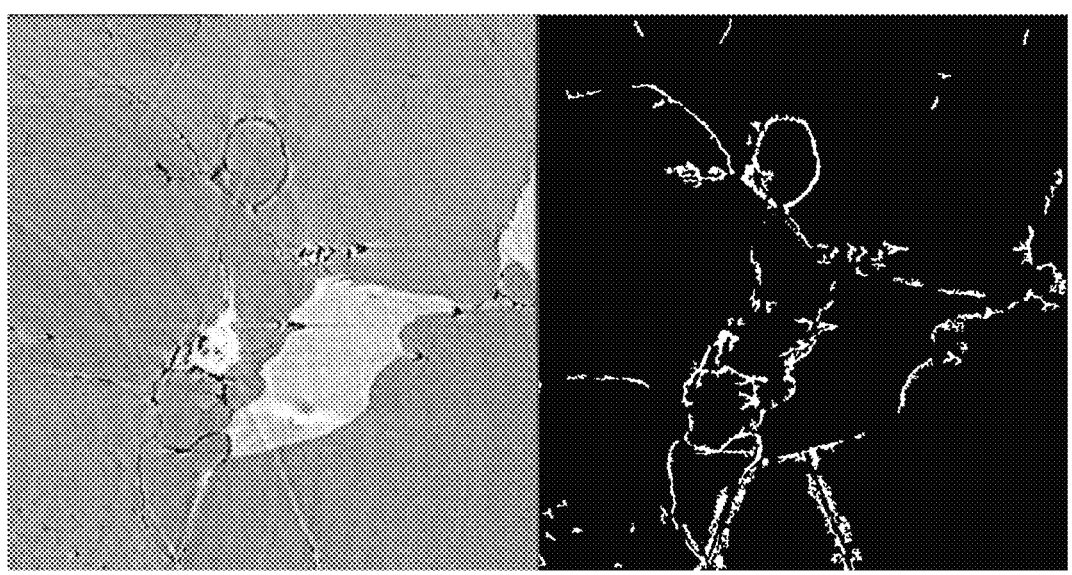
FIG. 4 is a schematic view of a 2D slice before and after binarization.

Preprocessing of the micro-CT images can be implemented by a variety of image processing software, where Avizo® software is the most common. First, a set of 3D CT images of rock samples are loaded into the image software, the original images being generally grayscale images. In the case of the image quality being not good enough, it may require smoothening and denoising of the images. Second, it is necessary to crop a desired part from the original data, or, to remove the non-sample part in the images. Image cutting is generally cut into a parallelepiped or cut into a cylinder. Third, it is necessary to transform the cut image into binary image. This step is called image segmentation, also known as binarization, which identifies the structure or material of interest, and interprets the rest as a matrix. The image after the segmentation only has two values, which are replaced with 0 or 1 in a computer, and the image display is converted to a black-and-white image, as shown in FIG. 4. The 3D images after the binarization can be seen in FIG. 2. There are many ways to segment the image, which are not introduced herein.

Statistically Analyzing of Basic Information

The purpose of this step is to obtain the basic information of the image, including: porosity, connectivity, and position, size, orientation, and anisotropy of each cluster. This information can be used for determining the values of the various parameters that require to be used in subsequent analysis steps. The implementation program is ctsta10.f90, written by the patent applicant Liu Jie.

In the basic information analysis process, it relates to a concept "cluster". A cluster is an independent structure composed of voxels of same material (e.g. void, with a material identity of 1) having a common surface for neighboring two voxels one by one in binary data. If an individual voxel is material 1, and there is not common plane with other voxels around that are material 1, then this voxel is a cluster. A plurality of voxels that are identified the same material can be connected by common planes one by one into a large and very complex cluster, such as a pore network in sandstone. A plurality of intersected cracks also constitute a cluster. In its original definition, a cluster may also be interpreted as a structure that is interconnected inside but not connected with an outside world. All voxels in one cluster have the same unique label different from labels in other clusters.

Among many parameters, the anisotropy of the pore is a key point, and the anisotropy is calculated by a method as follows:

for a cluster containing n voxels, each voxel forms a vector from a center point of the cluster to a current position i presented as $a_i=(a_{xi}, a_{yi}, a_{zi})^T$, and coordinates of a center of the cluster may be calculated by a mean value of all point coordinates in the cluster. Then an anisotropy of the structure can be represented by an orientation matrix R:

$$R = \sum_{i=1}^{n} a_i a_i^T = \begin{bmatrix} \sum_{i=1}^{n} a_{xi}^2 & \sum_{i=1}^{n} a_{xi}a_{yi} & \sum_{i=1}^{n} a_{xi}a_{zi} \\ \sum_{i=1}^{n} a_{xi}a_{yi} & \sum_{i=1}^{n} a_{yi}^2 & \sum_{i=1}^{n} a_{yi}a_{zi} \\ \sum_{i=1}^{n} a_{xi}a_{zi} & \sum_{i=1}^{n} a_{yi}a_{zi} & \sum_{i=1}^{n} a_{zi}^2 \end{bmatrix}$$

The matrix has three eigenvalues $\tau_1 < \tau_2 < \tau_3$, and corresponding eigenvectors $\mu_1, \mu_2, \mu_3$. An isotropic index $I=\tau_1/\tau_3$ and an elongation index $E=1-\tau_1/\tau_3$ are used to define the anisotropy of the pore. When $E \to 0$ and $I \to 1$, it indicates that the cluster is isotropic.

There are output files from the statistically analyzing of basic information, with each file recording different information of the image.

1) Basic information: provides the basic information of the image data, including porosity, specific surface area, number of the clusters (the cluster herein is the void structure within the sample), connectivity and other statistical information.

2) Particle/pore throat distribution.

3) Result of connectivity: simply lists all the information of percolating clusters in the current image, including their number and their percolating state. On the three directions of x, y, z, 0 represents not percolating, and 1 represents percolating.

4) Statistics of cluster size: provides cluster number, number of voxels contained in each cluster, equivalent radius square, total number of voxels contained by the current cluster, and cumulative percentage of total void voxels.

5) Shape of each cluster: provides information including cluster size, surface area, dimensions in principle directions, isotropy index, and elongation index.

6) Orientation matrix of each cluster: provides the center coordinates and orientation matrix of each cluster.

7) Normalized orientation matrix of each cluster: provides the normalized orientation matrix of each cluster and the direction angle of each eigenvector.

Filtration

The purpose of this step is to remove unimportant cluster in the model, making a subsequent calculation and analysis more convenient. Filters parameters that can be chosen include size, position, whether percolating, anisotropy, etc of the cluster.

For example, in general, natural samples contain a lot of tiny structures, representing small pores in the sample and noise generated when images are obtained. These small pores can be ignored in the crack analysis, so filtering these excessively small structures out contributes to the subsequent analysis.

The structural parameters obtained from the results of analysis process of the basic information provide the basis for determining filtering thresholds.

When any one cluster (structure) meets the filter condition, material identities of all voxels within the cluster will be modified, that is, modified from the original void identity 1 to 0, indicating that this small void structure transforms into a part of the rock, and is not exist in a subsequent analysis.

Figure 5:
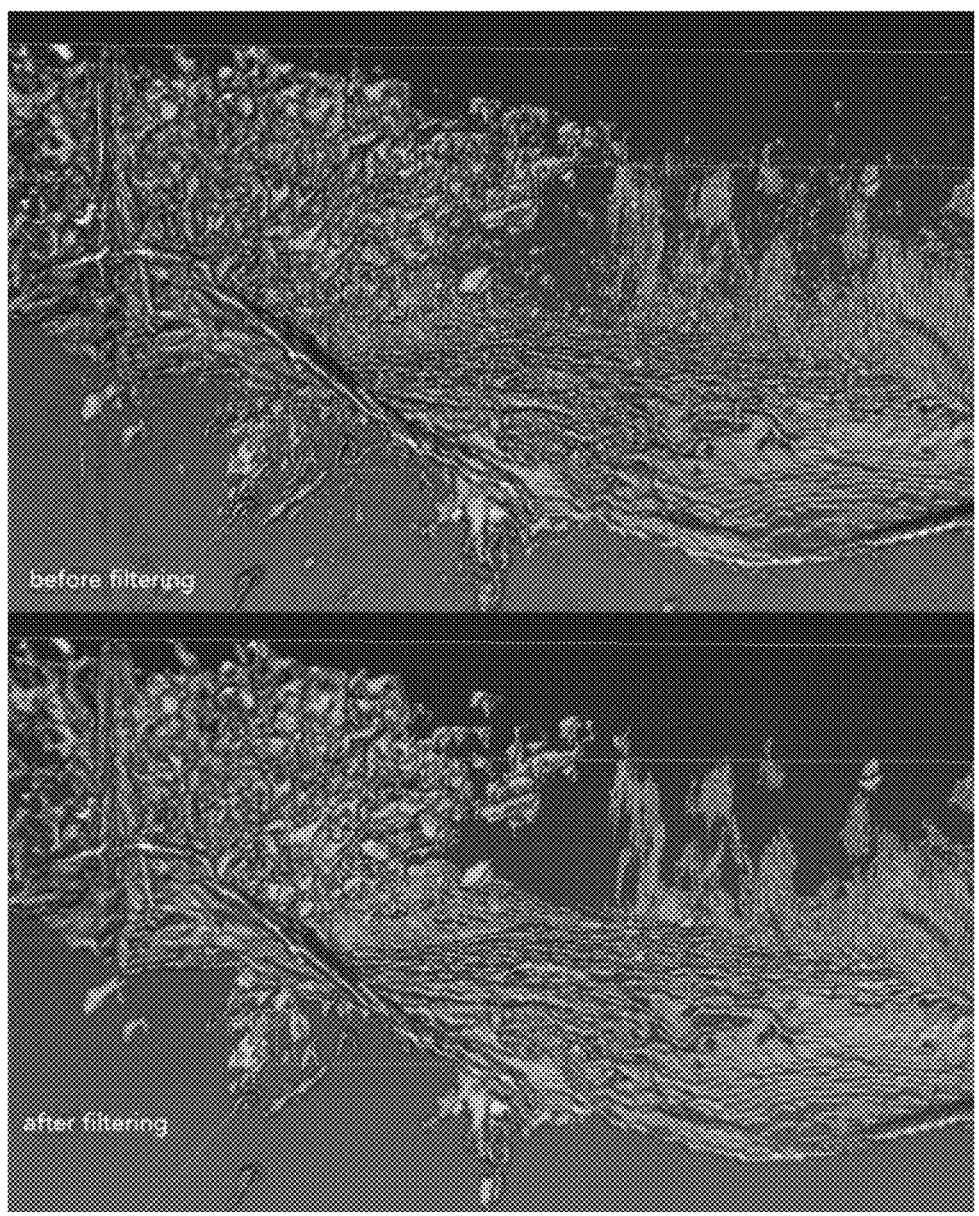
FIG. 5 is a comparison chart of a rock sample before and after filtration.

In addition to the case of tiny pores contained in the rock, there is also a case where a solid rock contained in the void structure is identified as 0. With regard to this, a file with opposite identity is generated by swapping the label in the data file (e.g. labmat=1−labmat), and the filtration is run again. After processing, the data needs to be reversed again and stored. FIG. 5 shows that excessively small voids and image noise are significantly suppressed after the filtration.

Smoothening

Filtered data serves as the input data of this step. As the complexity of the structure of the natural sample, the digital image that only has been filtered is still difficult to process, so in this step, the image is performed smoothening and mending operation, so that the image shape is as simple as possible and easy to process. The smoothening and mending of the image are realized by using the closing operation of mathematical morphology. The morphological closing operation includes a dilation operation and a following erosion operation.

Structuring element: can be any shape and size, and has a reference point called origin. In general, the structuring element refers to a square or a disc having an origin centered on a center, but other shapes may also be used.

Figure 6:
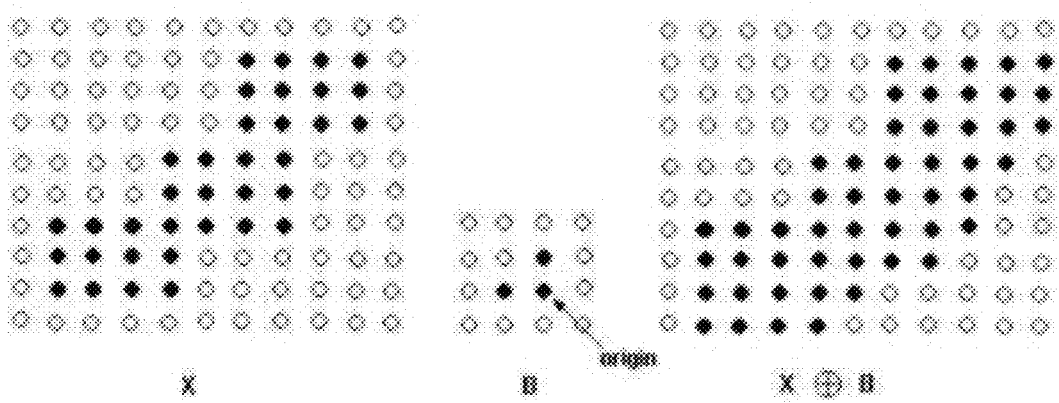
FIG. 6 is a process diagram of implement of dilation algorithm.

Dilation operation: a basic operation in morphology. It is essentially an operation to evaluate local maximum. A previously defined structuring element B is used to be convolved with an image A, that is, a maximum value of a gray scale of the pixel in a region of the image A covered by the structuring element B is calculated first, and the maximum value is assigned to a pixel specified by an origin of the structuring element B. This causes a highlighted area of the grayscale image to expand gradually. For a binary image, it is also equivalent to process an OR operation to the structuring element B and the image A, and a result of the operation determines a value of the pixel specified by the origin (FIG. 6).

Figure 7:
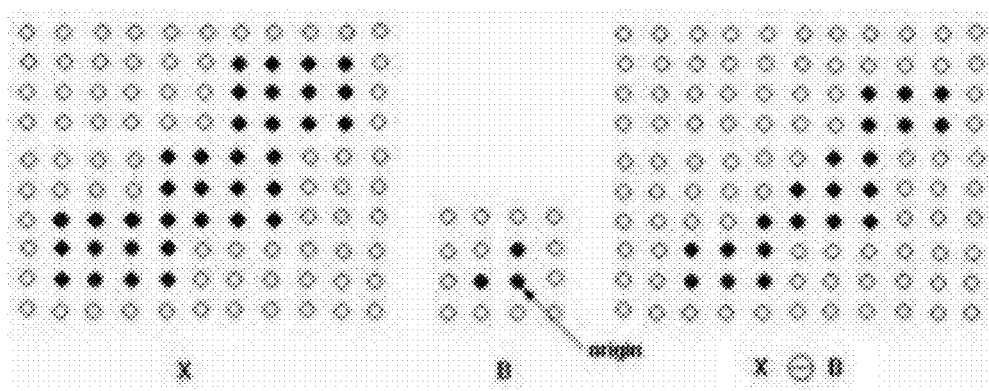
FIG. 7 is a process diagram of implement of erosion algorithm.

Erosion operation: a basic operation in morphology. Mutually dual to the dilation, erosion is essentially an operation to evaluate local minimum, having an operation method similar to the dilation, which uses the local minimum for assigning to a pixel specified by the origin of the structuring element B. This operation causes the highlighted area of the grayscale image to reduce gradually. For the binary image, it is also equivalent to process an AND operation to the structuring element B and the image A, and a result of the operation determines a value of the pixel specified by the origin (FIG. 7). Since the erosion and the dilation are mutually dual, a complementary set of the image A being eroded by the structuring element B equals to a complementary set of the image A being dilated by the structuring element B.

Figure 8:
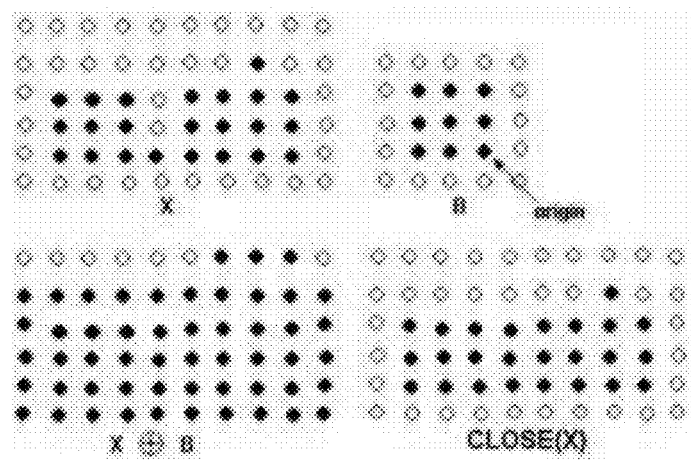
FIG. 8 is a process diagram of implement of closed operation.

Closing operation: a dilation operation is processed to the image first, and then an erosion operation is processed. Generally, the closing operation may fill small pores and close little cracks, and an overall position and shape of the image remain the same (FIG. 8).

Figure 9:
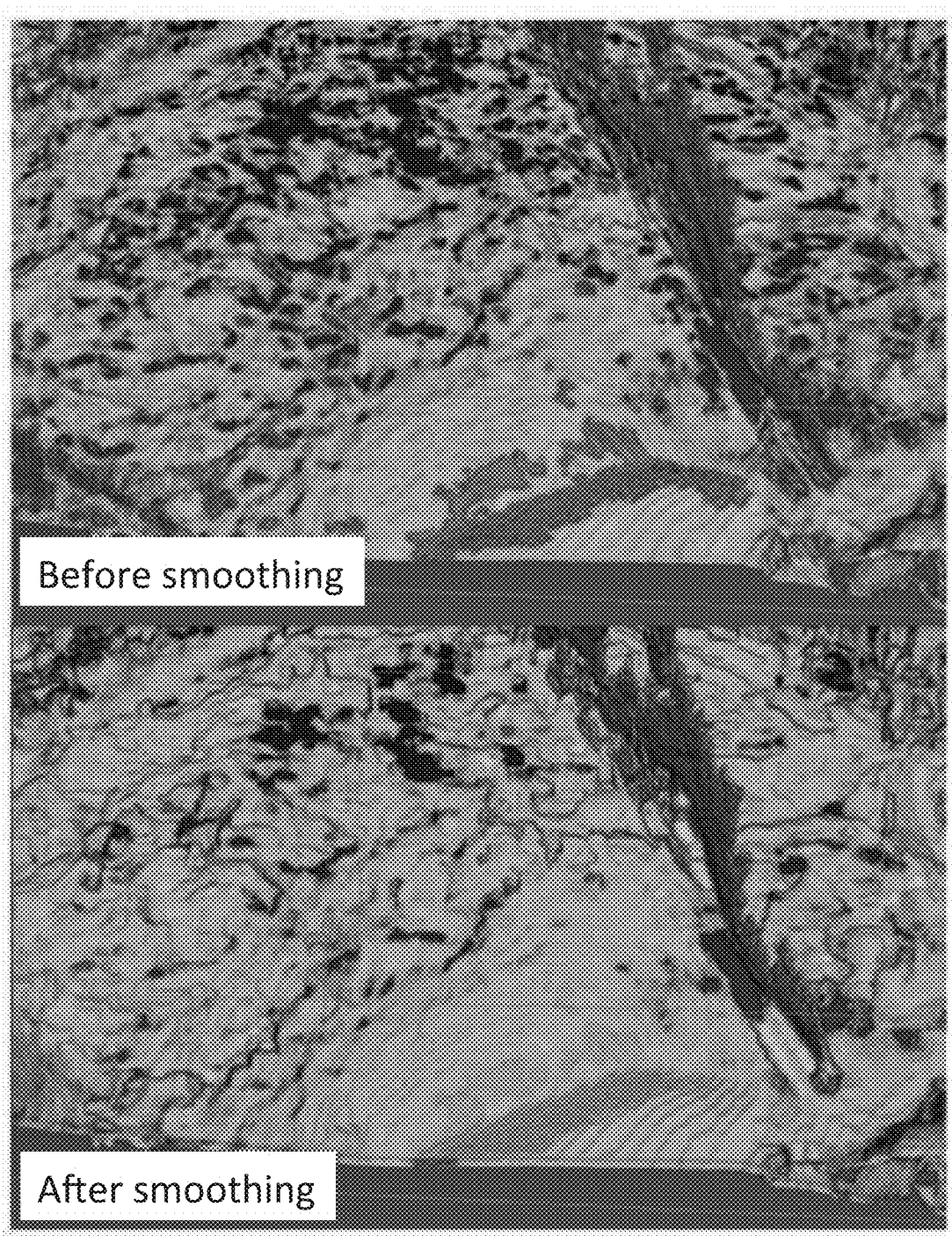
FIG. 9 is a schematic view of the smoothening effect.

In the processing of 3D data, the structuring element is changed from square and disc to cube and sphere accordingly. Different shapes and sizes of the structuring element produce different processing results, and thus the structuring element should be larger than the size of all noise blocks to be removed. It also can increase times of the dilation and erosion, such as multiple erosions after multiple dilations, to make the smoothening effect better. However, it should be noted that the structuring element that is too large and erosion after multiple dilations may remove some features of the original image, and thus multiple attempts should be performed to select appropriate type, size of the structuring element, and the number of operations based on the processing effect (FIG. 9).

Thinning

For crack analysis, the image is required to be processed using thinning algorithm, and a figure that is approximate to the shape of original object and consists of simple curved surfaces is obtained.

The thinning algorithm proposed in the present embodiment is somewhat similar, but not identical, to the morphological thinning algorithm in 2D image processing. It should be noted that, the present invention processes 3D data. If the 3D image is processed only from a 2D perspective, it is necessary to regard the 3D image as a set of 2D images and to adopt a 2D method to each 2D slice. However, since the performance of the 3D image in 2D slices is not stable, even if they are adjacent slices, there may be a case that the difference is relatively large. If two 2D slices are used thinning algorithm alone, the image in the two slices will be staggered so that an original structure in the three dimensions is misinterpreted into two separate structures. In addition, if the 3D image is processed only from the 2D perspective, it means that the slices on the three directions are required to be processed simultaneously, and results of the slices on the three directions after processing will inevitably exist inconsistencies. How to synthesize the results of the three directions is also a very thorny problem. Therefore, the thinning method commonly used in 2D image is not applicable herein.

Figure 10:
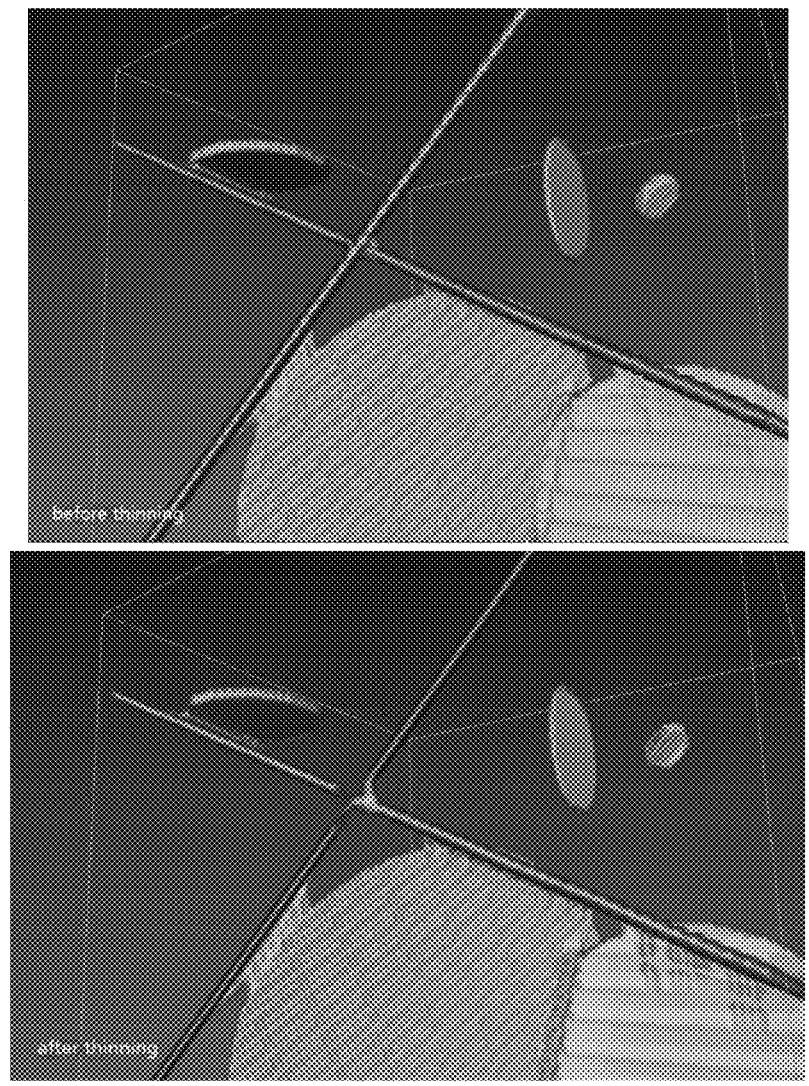
FIG. 10 is a comparison chart before and after thinning.

The thinning algorithm proposed in the present embodiment is performed from a 3D perspective. Firstly, a current point is determined whether a void point needed to be processed. For the void point, its extension in the three directions is calculated, that is, checked point by point in the three directions of x, y, z. If a non-void point is encountered on one of the directions, the check on that direction is stopped and an extension length is recorded. After the three directions are finished checking, the direction with smallest extension length is selected as the direction to be thinned. Then this direction is thinned from the boundary to the center to a thickness of d (d could be any number and recommended to be 2 or 3) voxels. Except the d (2 or 3) voxels, assignments of other voxels on this direction are all changed during this process, making them a part of the rock, and recording relevant information (thinning direction and thinning voxels) (FIG. 10). After the processing is completed, calculation of a next point is performed. It should be noted that, thinning is a manner to facilitate the processing of the image, in the subsequent steps, the thinning information recorded here will be used to restore the thinned pore.

Separation

This is the key to the present invention. This step takes the data that is thinned in the last step as an input, and perform the separation to the void structure in the image according to a series of pre-defined conditions, so that the originally intersected structure is separated into independent structures.

In this step, firstly, each cluster is numbered according to how many voxels are contained, and the largest structure is numbered as 1. Then spatial dimensions occupied by each structure in the 3D space, i.e., a minimum coordinates and a maximum coordinates of the structure spanned in three directions of x, y, z, are calculated separately. Next, in order to avoid being affected by other structures, each void structure will be processed separately, and the space to be processed is the rectangular space constituted by the minimum coordinates and the maximum coordinates on the 3D directions. Search space of the process is less than the original data space, which will greatly save the running time of the program.

The specific processing step is divided into two parts.

Figure 11:
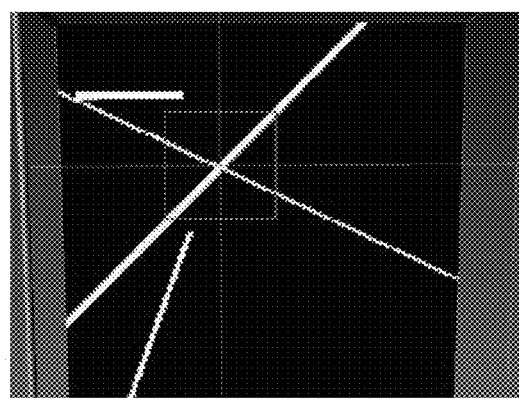
Figure 11:
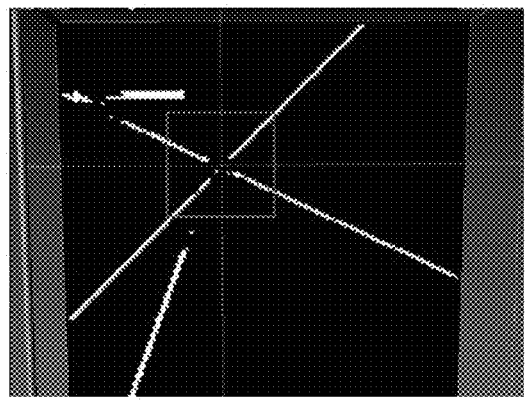

The first part uses local grids for processing point by point from three-dimensions. Two 2D square local grids are generated, with a current processing pixel as a center, and two given analysis radiuses (actually, half-side-lengths of square grids), a large one and a small one, and each point-by-point process uses only image information in the grid. The current processing pixel is taken as an origin, with two local grids being divided into four quadrants by the origin. If for the local grids with large radius, two void structures in any two quadrants are linear and the angle between them meet a pre-defined criterion (an adjustable input parameter), and for the local grid with small radius there are a number of void voxels (also an adjustable input parameter) contained in a corresponding quadrant, then they are taken as a projection of two cracks with different intersecting directions on a current section, thus changing a pixel value at the current origin, making it a part of the rock (FIG. 11A and FIG. 11B). The reason why using the two radiuses, an inner one and an outer one, as the criteria for determining is that, if the small grid contains too few number of void voxels, the calculated orientation of void will be unreliable. Therefore, we use the local grid with the larger radius to determine the orientation of the image, while use the grid with the smaller radius to avoid a phenomenon of too much removal caused by the large radius.

Since the processed image is 3D, the above processing steps will be performed sequentially from three directions until it is determined whether the current pixel should be classified as the rock. After this step, most of the intersected void structures can be broken into two or more independent void structures. The effect of disconnection depends on the void structure and parameter setting. It is recommended to test multiple times and select appropriately parameters based on the testing results. For example, when the outer radius is too large, it causes the range of disconnected voxels too large and damages the structure. When the radius is too small, the number of the void voxels contained in a very small grid may be too few, and the calculated anisotropy is unreliable. The range of the intersected angle is also necessary to be defined. In the present embodiment, an angle between the two structures can be regarded as approximately parallel when it is 0° to 30° and 150° to 180°, and the structures have an angle between 30° and 150° are considered as different intersected crack structures.

In the first part, if the number of the void voxels contained in the current local grid is few, it is possible that the void voxels are not forming a linear structure, so that intersection points are not removed in the first part. Thus there is a possibility that some of large intersected cracks are still connected by only a few voxels and keeping an interconnected cluster. This situation was not processed well in the first part, and it needs to be processed in the second part.

In the second part, it is also processed from three directions, but no longer point-by-point processing, but slice-by-slice processing. The space occupied by the current analyzed cluster is divided into a plurality of non-overlapping cubic sub-volumes, and then each sub-volume is analyzed slice by slice. In a small cube, the anisotropy of the void structure of a first slice of the 3D local grid is first analyzed along a Z-axis direction, and the is determined whether it is linear, and then the anisotropy of the void structure of a next slice is calculated and is determined whether it is linear. If the images of two adjacent slices are linear and their anisotropies have large difference, that is, the adjacent layers are not approximately parallel, then they are considered as different pore structures, and all the points in the second slice belonging to void are identified as a rock type, making the different void structures no longer in contact. The program then continues to use the same method to process the next two adjacent slices of image until the last slice. Then this implementation is repeated from a Y-axis direction and an X-axis direction, respectively. When it is all completed, an analysis of a next 3D sub-volume is performed.

Figure 12A:
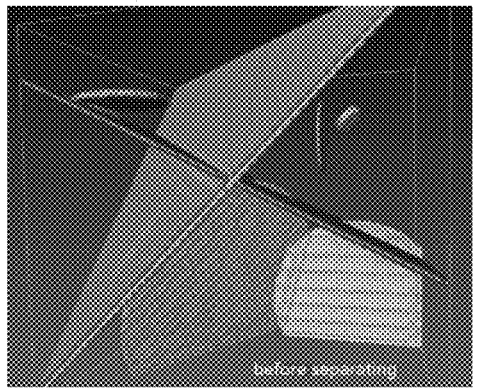
FIG. 12A is a comparison chart before separation.
Figure 12B:
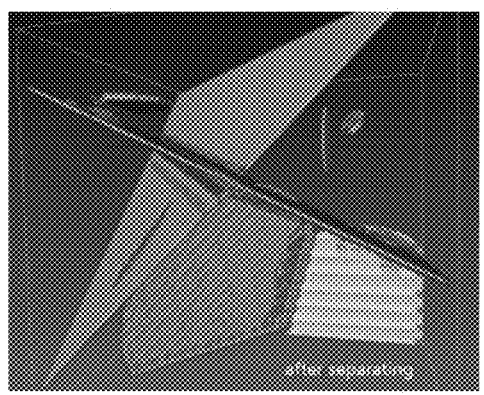
FIG. 12B is a comparison chart after separation.
Figure 13:
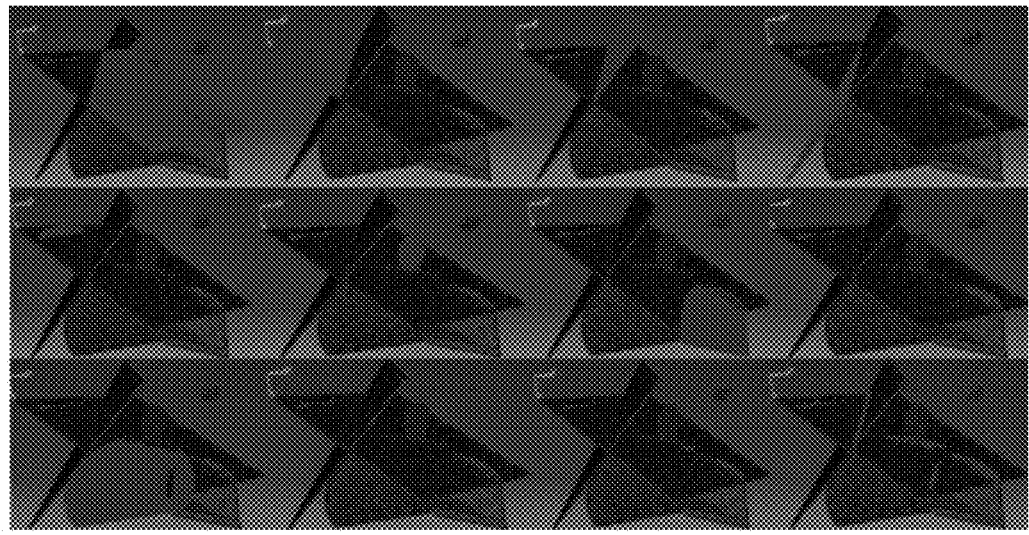
FIG. 13 is individual structure diagram after separation.

The results of these two parts of separation operation are shown in FIG. 12A, FIG. 12B and FIG. 13.

The principle of the algorithm used to calculate the image direction in the local grid in this step is the same as that of the calculation of the 3D direction matrix R (see statistically analyzing basic information), and in case of two-dimensions, there is accordingly:

$$R = \sum_{i=1}^{n} a_i a_i^T = \begin{bmatrix} \sum_{i=1}^{n} a_{xi}^2 & \sum_{i=1}^{n} a_{xi} a_{yi} \\ \sum_{i=1}^{n} a_{xi} a_{yi} & \sum_{i=1}^{n} a_{yi}^2 \end{bmatrix}$$

The matrix has two eigenvalues $\tau_1 < \tau_2$, and corresponding eigenvectors $\mu_1$, $\mu_2$. An isotropic index $I = \tau_1 / \tau_2$.

The value of I is used to determine whether the projection of the void in the two-dimensions is linear. The two eigenvectors of the matrix can be calculated and their directions represent the angles between principle axes of the structure in this quadrant with the x-axis and y-axis, respectively, i.e., the direction of void structure can be determined.

Figure 14:
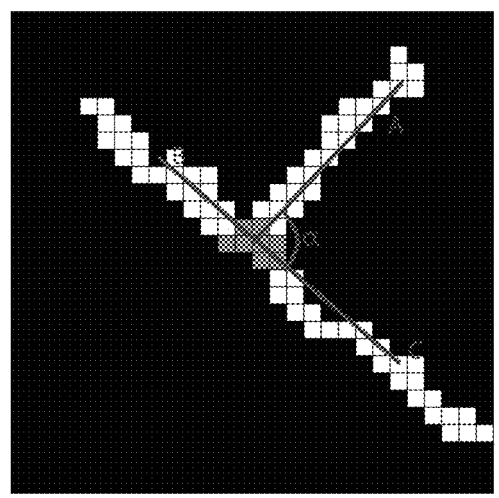
FIG. 14 is a schematic view of T-type intersection.

Three typical cases often appear in the actual processing of the image are as follows:

1) as shown in FIG. 14, when the cracks are two T-type intersecting cracks, using one voxel in the central blue part as an origin, the entire cluster is considered as consisting of three parts: a first quadrant A, a second quadrant B and a fourth quadrant C. The program will calculate the orientation matrix of A, B, and C, respectively. When the number of the void voxels around the origin is enough, the angles between A, B and C will continue to be calculated. If there is a cosine value of the angle having an absolute value less than a given threshold, then it means that there is an intersection situation that angles between A, B, and C is relatively large, and the void voxel at the origin needs to be changed to a rock voxel.

Figure 15:
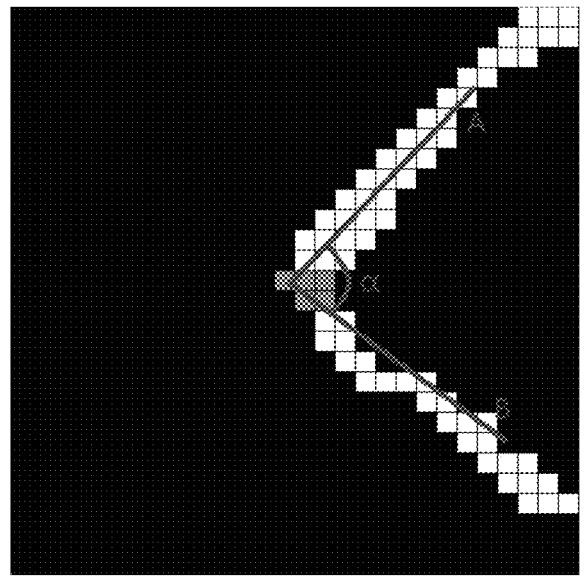
FIG. 15 is a schematic view of turn-type intersection.

2) When the crack is that shown in FIG. 15, the crack appears a large angle transition, which can also be considered as two cracks are connected, and needed to be disconnected. Using a voxel of the central blue part as an origin, the entire cluster is considered as consisting of two parts: a first quadrant A and a fourth quadrant B. The program will calculate the orientation matrix of A and B, respectively. When the number of the void voxels around the origin is enough, the angle between A and B will continue to be calculated. If there is a cosine value of the angle having an absolute value less than a given threshold, then it means that A and B belong to an intersection situation that the angle is relatively large, and the void voxel at the origin needs to be changed to the rock voxel.

Figure 16:
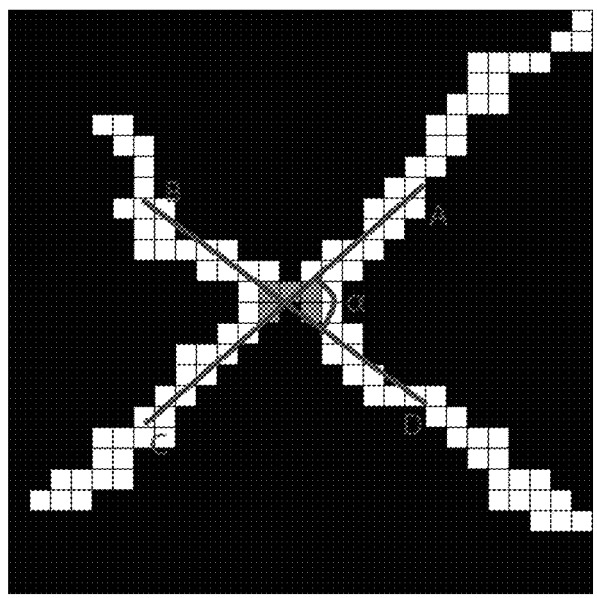
FIG. 16 is a schematic view of cross-shaped intersection.

3) When the cracks are cross-shaped intersected shown as FIG. 16, using a voxel in the central blue part as an origin, the entire cluster is considered as consisting of four parts: a first quadrant A, a second quadrant B, a third quadrant C, and a fourth quadrant D. The program will calculate the orientation matrix of A, B, C and D, respectively. When the number of the void voxels around the origin is enough, the angles between A, B, C and D will continue to be calculated. If there is a cosine value of the angle between any of two of them having an absolute value less than a given threshold, it means that they belong to an intersection situation that the angle is relatively large, and the void voxel at the origin needs to be changed to the rock voxel.

Combination

This step takes the result of the last step as an input data, and is a correction of the previous steps. That is, for the actually elongated cracks, they are disconnected in the separation process. Through this step, they are combined into a cluster, this step also includes processing some small clusters generated during the separation, and restoring the crack to a state before being thinned.

Firstly, the structures in image is labeled. Since after the separation step, the image this time will contain more clusters than before. After completing labeling, the determination of whether each void structure should be combined with another void structure begins, with determining conditions including: i) whether normal directions of the two void structures are approximately parallel; ii) whether they originally belong to the same void before the separation step; iii) whether their normal lines are perpendicular to a line of their centers. If the above three conditions are satisfied, then they are determined as should be combined.

Figure 17:
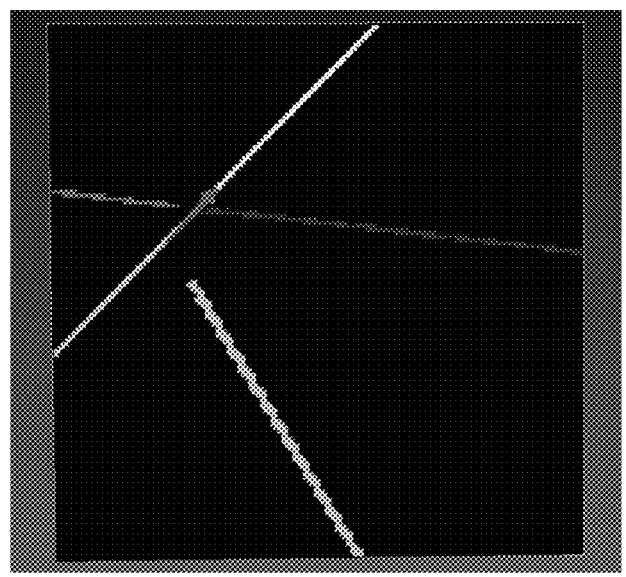
FIG. 17 is a process diagram of combination.

The combination operation includes re-labeling a supplier cluster number as a receiver cluster number, re-counting the total number of voxels contained in the two clusters, and recording the receiver cluster number, so that the supplier cluster is incorporated into the receiver cluster. During the program is running, the following situation may be encountered: the cluster used as the receiver is also used as the supplier and has been incorporated into other clusters. At this point, the receiver number recorded in the combination before is required to find the receiver cluster, and this pore is received and combined as a new receiver (FIG. 17).

Figure 18:
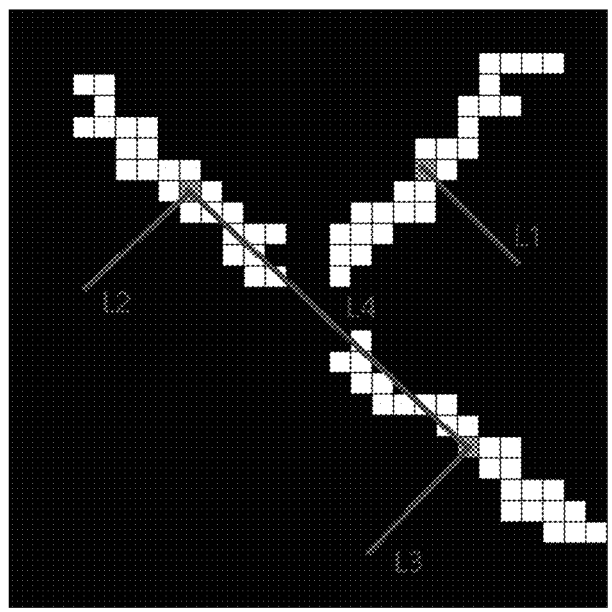

As shown in FIG. 18, due to the separation algorithm, the cracks originally belong to the same cluster are now divided into three, and the central part has been changed to the rock, that is, black voxel. For these three independent cracks, their normal lines are L1, L2 and L3, respectively, and L4 is a line of centers of two of the cracks. Since the normal line L1 is not approximately parallel to L2 and L3, the crack of it is firstly determined as being not combined with the other two cracks. L2 and L3 are approximately parallel, and then continue to determine whether the line of the centers of the two cracks is perpendicular to their normal lines. It can be seen from the figure that, L4 is approximately perpendicular to L1 and L2, the two cracks originally belong to the same cluster, and thus they are determined as can be combined.

Figure 19:
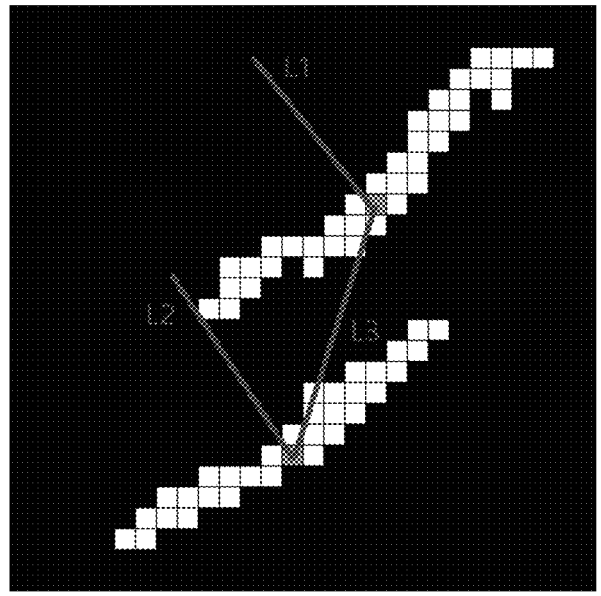
FIG. 19 is a schematic view of a typical case 2.

In the case shown as FIG. 19, the normal lines L1 and L2 of the two cracks are parallel, but the line L3 of their centers does not form as approximate perpendicular to L1 and L2, so the two cracks in this figure cannot be combined.

Since the separation process may produce some smaller fragmentary voids (such as the last picture of FIG. 15), these voids often do not have a clear orientation because of their small size, and thus they cannot be calculated their normal directions, thereby the above combination operation being difficult to be properly handled. Therefore, they are incorporated into the larger void structure by using a method of calculating between-class distance. Respective center points of these small voids are taken as representing their coordinates, minimum distances between them to the voxels of other pores are calculated in turn, and a larger void that is nearest is selected for incorporating the small void.

Figure 20A:
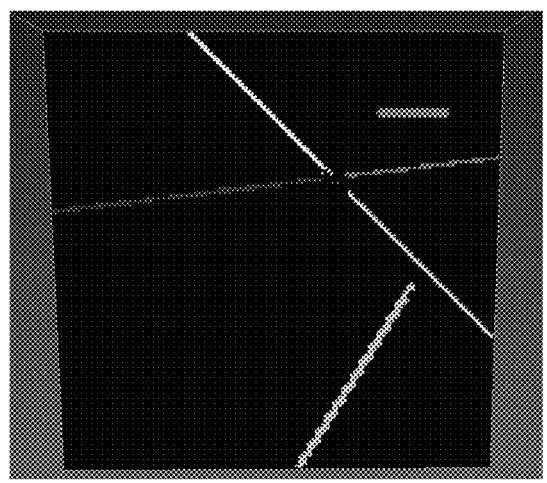
FIG. 20A and FIG. 20B are comparison charts before and after combination (shown in a two dimensional plane).
Figure 20B:
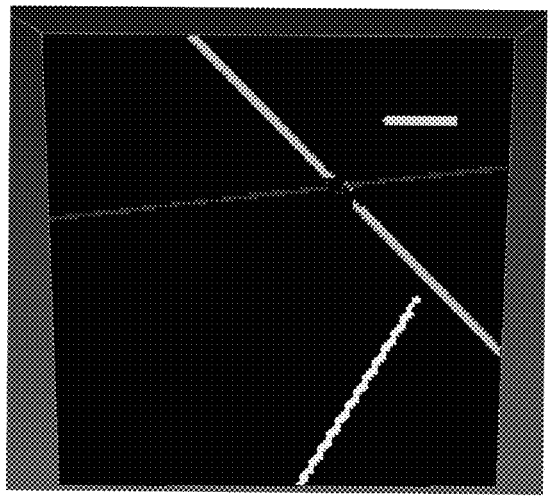
Figure 21:
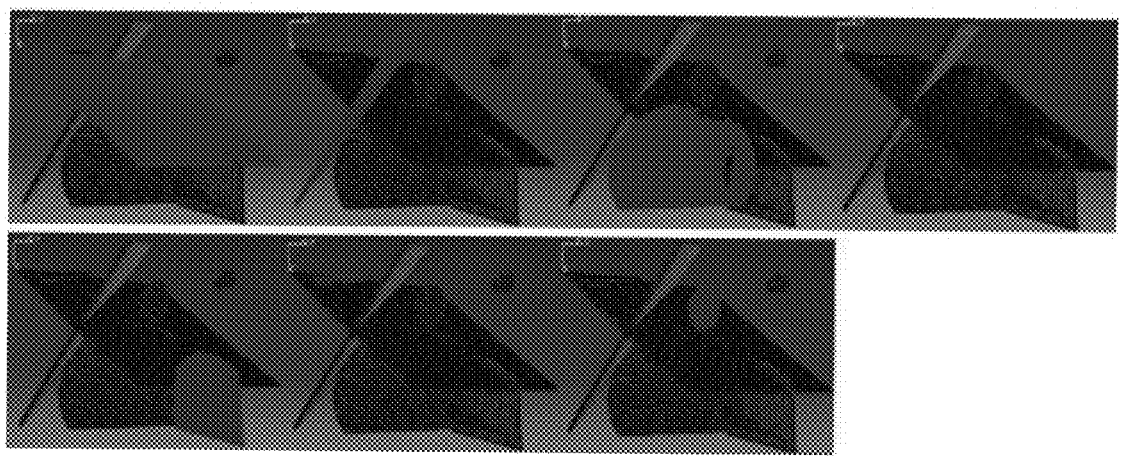
FIG. 21 is a schematic view in turn of each structure after the combination.

Finally, the shape of each pore is restored to that before being thinning using the information recorded in the thinning step. A final result can be obtained (FIGS. 20A, 20B and 21).

Characterization of Cracks

After completing all the processing, characterization of cracks is performed. Herein, only testing data shown in FIG. 13 is taken as an example, and major results are given in tables. Table 1 shows that the number of voxels contained in the processed data is reduced, which is due to change of identity values of some voxels during the separation of cracks, and the increase in surface area is also due to the disconnection of the intersecting cracks. There are only 3 clusters before the separation, and there are 8 clusters after the separation and identification. The change of size and morphological parameters of the cluster is very obvious. Data in Table 3 provide statistical characteristics of the length and width of each crack in the model. More information can be extracted from the 7 output files of ctsta10.f90.

TABLE 1 comparison of main parameters before and after separation and identification of cracks

| Parameter | Before separation | After separation |
|---|---|---|
| porosity | 3.18 | 2.847% |
| surface area | 177856 | 177346 |

TABLE 2 comparison of cluster size before and after separation and identification of cracks

| | NO. | SIZE | RS^2 | ACCUPORE | PERCENT | |
|---|---|---|---|---|---|---|
| | | | | 3 | | |
| before separation .clus | 1 | 105891 | 4599.26 | 105891 | 0.98479 | A total of 3 clusters, one of which accounted for 98.5% of porosity. |
| | 2 | 927 | 32.56 | 106818 | 0.99341 | |
| | 3 | 709 | 112.88 | 107527 | 1.00000 | |
| | | | | 8 | | |
| after separation .clus | 1 | 38309 | 4107.55 | 38309 | 0.39865 | Containing 8 clusters (structure). |
| | 2 | 30234 | 3524.90 | 68543 | 0.71327 | |
| | 3 | 13378 | 1490.33 | 81921 | 0.85248 | |
| | 4 | 10017 | 683.37 | 91938 | 0.95672 | |

TABLE 2-continued comparison of cluster size before and after separation and identification of cracks

| NO. | SIZE | RS^2 | ACCUPORE | PERCENT |
|---|---|---|---|---|
| 5 | 2946 | 170.90 | 94884 | 0.98738 |
| 6 | 447 | 111.62 | 95331 | 0.99203 |
| 7 | 701 | 33.84 | 96032 | 0.99932 |
| 8 | 65 | 24.20 | 96097 | 1.00000 |

TABLE 3 comparison of cluster form before and after separation and identification of cracks

| | Cluster | Voxels | Surface | Dim-1 | Dim-2 | Dim-3 | Iso-index | Elong-index | |
|---|---|---|---|---|---|---|---|---|---|
| before separation .out2 | 1 | 105891 | 175392 | 133.00 | 146.35 | 185.69 | 0.716 | 0.212 | The first cluster has similar dimensions in three directions, and the isotropic index is > 0.7 |
| | 2 | 927 | 922 | 5.49 | 15.59 | 15.75 | 0.349 | 0.010 | |
| | 3 | 709 | 1542 | 1.00 | 30.05 | 30.05 | 0.033 | 0.000 | |
| after separation .out2 | 1 | 30234 | 70439 | 2.05 | 172.83 | 189.33 | 0.011 | 0.087 | All clusters have a low isotropic index, indicating that the structure is in crack morphology. |
| | 2 | 38309 | 60716 | 2.62 | 165.17 | 170.62 | 0.015 | 0.032 | |
| | 3 | 13378 | 28887 | 1.96 | 92.51 | 123.63 | 0.016 | 0.252 | |
| | 4 | 10017 | 11414 | 3.07 | 69.21 | 78.32 | 0.039 | 0.116 | |
| | 5 | 2946 | 2698 | 3.28 | 31.58 | 41.55 | 0.079 | 0.240 | |
| | 6 | 701 | 1526 | 1.00 | 29.88 | 29.88 | 0.033 | 0.000 | |
| | 7 | 447 | 1200 | 5.42 | 14.43 | 17.43 | 0.311 | 0.172 | |
| | 8 | 65 | 211 | 2.10 | 6.37 | 18.50 | 0.114 | 0.655 | |

The 3D binary image with voxel as the basic unit can be performed the separation, identification and characterization of the cracks by six steps, basic characteristic analysis, filtering, smoothening, thinning, separation and combination. This technique provides important supports for researches such as crack morphology, permeability and mechanical response, and scaling up.

The above-described implementations of the present invention do not constitute a limitation to the scope of protection of the present invention. Any modifications, equivalent substitutions and improvements within the spirit and principle of the present invention shall be all included in the scope of protection of the claims of the present invention.

What is claimed:

1. A method of separating, identifying and characterizing cracks in three-dimensional (3D) space for a digital volumetric image, the method comprising:

preprocessing the digital volumetric image, the digital volumetric image comprised of voxels;

statistically analyzing basic information of the digital volumetric image to determine a plurality of void structures in the digital volumetric image, wherein the basic information includes porosity, connectivity, and position, size, orientation and anisotropy of each of the plurality of void structures;

determining one or more unnecessary void structures of the plurality of void structures in the digital volumetric image based on a filtering condition, and removing the unnecessary void structures from the digital volumetric image;

smoothening and mending the digital volumetric image;

determining three extension lengths in three directions x, y and z of a 3D coordinate system for each of the plurality of void structures, wherein each of the extension length is a length, in voxels, from one to another void-solid boundary of the corresponding void structure in the corresponding direction, and thinning each of the plurality of void structures in the direction x, y, or z in which the extension length is the shortest within the three extension lengths of the corresponding void structure;

analyzing the voxels of the digital volumetric image to separate each of the plurality of thinned void structures into a plurality of cracks, the plurality of cracks corresponding to an intra-connected structure of cracks in a crack network; and combining disconnected cracks of the plurality of cracks to form a first crack within the plurality of cracks, combining fragmentary cracks of the plurality of cracks to form a second crack within the plurality of cracks, and restoring a thickness of each crack of the plurality of cracks.

2. The method of separating, identifying and characterizing the cracks in the 3D space according to claim 1, wherein the step of statistically analyzing basic information of the digital volumetric image to determine a plurality of void structures in the digital volumetric image comprises statistically analyzing the anisotropy of each of the void structures in the digital volumetric image, comprising:

determining the anisotropy of a void structure among the plurality of void structures, wherein a void structure contains n voxels, each of the n voxels forms a vector from a center point of a cluster to a current position i presented as $a_i = (a_{xi}, a_{yi}, a_{zi})^T$, coordinates of a center of the void structure is calculated by a mean value of a plurality of coordinates in the void structure, and the anisotropy of the void structure is represented by an orientation matrix R:

$$T = \sum_{i=1}^{n} a_i a_i^T = \begin{bmatrix} \sum_{i=1}^{n} a_{xi}^2 & \sum_{i=1}^{n} a_{xi}a_{yi} & \sum_{i=1}^{n} a_{xi}a_{zi} \\ \sum_{i=1}^{n} a_{xi}a_{yi} & \sum_{i=1}^{n} a_{yi}^2 & \sum_{i=1}^{n} a_{yi}a_{zi} \\ \sum_{i=1}^{n} a_{xi}a_{zi} & \sum_{i=1}^{n} a_{yi}a_{zi} & \sum_{i=1}^{n} a_{zi}^2 \end{bmatrix},$$

wherein the matrix R has three eigenvalues $\tau_1 < \tau_2 < \tau_3$ corresponding to eigenvectors $\mu_1$, $\mu_2$, $\mu_3$, an isotropic index $I = \tau_1/\tau_3$ and an elongation index $E = 1 - \tau_1/\tau_3$, are used to define the anisotropy of the void structure, and the void structure is isotropic when $E \rightarrow 0$ and $I \rightarrow 1$, wherein the cluster is a voxel made of a material when the voxel is not connected by common planes with other voxels made of the material in binary data, or a plurality of voxels made of the material when the each of the voxels are connected by common planes one by one in binary data, wherein the cluster is independent, interconnected inside, and constituted by a single crack or a plurality of intersected cracks as the voxels are interconnected.

3. The method of separating, identifying and characterizing the cracks in the 3D space according to claim 2, wherein determining the one or more unnecessary void structures of the plurality of void structures in the digital volumetric image based on the filtering condition and removing the unnecessary void structures from the digital volumetric image, to filter the digital volumetric image comprises:

modifying material identity of the void structure by modifying each void identity of the voxels in the cluster from 1 to 0 in the digital volumetric image, wherein the void identity 1 represents the void structure and identity 0 represents a part of a rock, wherein the cluster is removed from a subsequent analysis when the material identity of the voxels in the cluster is modified from 1 to 0.

4. The method of separating, identifying and characterizing the cracks in the 3D space according to claim 3, wherein smoothening and mending the digital volumetric image comprises:

performing smoothening and mending operations to the filtered digital volumetric image by applying morphological closing operation, which comprises of a dilation operation followed by an erosion operation, wherein the dilation operation is a basic operation in morphology for evaluating a local maximum of the image covered by a structuring element and assigning the maximum value to the voxel overlapped with the origin of the structuring element, wherein the erosion operation is a basic operation in morphology for evaluating a local minimum of the image covered by the structuring element and assigning the minimum value to the voxel overlapped with the origin of the structuring element, wherein the structuring element is a shape used to interact with the image, has a point of reference, called origin, usually locates at the center of the shape, wherein after a closing operation, small void structures in the image are filled, while an overall shape and position of the image remain the same.

5. The method of separating, identifying and characterizing the cracks in the 3D space according to claim 4, wherein determining the three extension lengths in the directions x, y and z of the 3D coordinate system for each of the plurality of void structures and thinning each of the plurality of void structures in the direction x, y, or z in which the extension length is the shortest within the three extension lengths of the corresponding void structure comprises:

determining whether a current point is a void point to be processed;

calculating extension lengths of the void point in three directions x, y, z by checking point by point on both sides, a positive side and a negative side, in each of the three directions x, y, z, wherein when a non-void point is encountered in one of the directions, the check in the one of the directions stops and an extension length is recorded;

selecting a direction with a smallest extension length as a direction to be thinned, and thinning the direction with the smallest extension length from the boundary to the center to a thickness of d, wherein d is a small positive integer and recommended to be 2 or 3;

changing the assignments of all the voxels except the d voxels to 0 in the direction with the smallest extension length, such that the voxels except the d voxels are a part of the rock;

recording information including the thinning direction and the thinning voxels; and proceeding to a next point after completing the processing of the current point.

6. The method of separating, identifying and characterizing the cracks in the 3D space according to claim 5, wherein analyzing the voxels of the digital volumetric image to separate each of the plurality of thinned void structures into the plurality of cracks comprises: separating the thinned data as a process of separation, so that the originally intersected structures are separated and become independent structures, the process of separation comprises:

using 2D squared local grids for point-by-point process from the three dimensions;

generating two 2D square local grids in the three directions, respectively, with a current processing voxel as a center, wherein the 2D squared local grids of one-voxel thick slice in 3D image include two analysis side-lengths having a large side-length and a small side-length, wherein each point-by-point process uses only image information in the grids;

taking the current processing voxel as an origin, and dividing the two local grids into four quadrants by the origin, wherein if two void structures in any two quadrants are linear and an angle between the two void structures meets a pre-defined criterion for the local grid with the large side-length, and if a number of void voxels contained in a corresponding quadrant is not less than a preset number for the local grid with the small side-length, then the two void structures are a projection of two cracks with different intersecting directions on a current section, the material identity of the voxel at the current origin is changed and the voxel is made into a part of the rock, determining whether the current processing voxel should be classified as a part of the rock by proceeding the processing step in the three directions in turn for a 3D image.

7. The method of separating, identifying and characterizing the cracks in the 3D space according to claim 6, wherein combining the disconnected cracks of the plurality of cracks to form the first crack within the plurality of cracks, combining the fragmentary cracks of the plurality of cracks to form the second crack within the plurality of cracks, until all fragmentary cracks have been combined with another crack or confirmed to be an independent crack, and restoring the thickness of each crack of the plurality of cracks comprises:

determining whether one of the plurality of the void structures is to be combined with another one of the plurality of the void structures according to three conditions of a determining criteria, wherein the three conditions of the determining criteria comprise:

determining whether normal directions of two void structures of the plurality of void structures are parallel;

determining whether the two void structures originally belong to the same void structure before the separation step;

determining whether normal lines of the two void structures are perpendicular to a line connecting centers of the two void structures, and combining the two void structures when the three conditions of the determining criteria are satisfied, the combined void structure can be combined with other void structures further if the three conditions are satisfied, wherein, after the combination of the two or more void structures, the cluster is comprised of several pieces of the cluster and represents one of the plurality of cracks, restoring the void structure to the original thickness before the thinning step, based on the information recorded in the thinning step.

8. The method of separating, identifying and characterizing the cracks in the 3D space according to claim 7, further comprising:

analyzing the porosity, the connectivity, and the position, the size, the orientation and the anisotropy of each of the plurality of cracks; and finishing the separation, identification and characterization of the cracks in the 3D space.

\* \* \* \* \*